United States Patent [19]

Sierra et al.

[11] Patent Number: 5,496,332
[45] Date of Patent: Mar. 5, 1996

[54] WOUND CLOSURE APPARATUS AND METHOD FOR ITS USE

[75] Inventors: Rolando Sierra, Miami; Lawrence A. Weinstein, Davie, both of Fla.

[73] Assignee: Cordis Corporation, Miami Lakes, Fla.

[21] Appl. No.: 326,465

[22] Filed: Oct. 20, 1994

[51] Int. Cl.⁶ .................................. A61B 17/04
[52] U.S. Cl. .............. 606/139; 606/144; 606/148; 606/213
[58] Field of Search ................... 606/139, 144, 606/148, 146, 213, 215

[56] References Cited

U.S. PATENT DOCUMENTS

| | | | |
|---|---|---|---|
| 4,602,635 | 7/1986 | Mulhollan et al. | 128/334 R |
| 4,890,612 | 1/1990 | Kensey | 606/213 |
| 4,890,615 | 1/1990 | Caspari et al. | 606/146 |
| 4,923,461 | 5/1990 | Caspari et al. | 606/146 |
| 4,935,027 | 6/1990 | Yoon | 606/146 |
| 5,015,250 | 5/1991 | Foster | 606/147 |
| 5,037,433 | 8/1991 | Wilk et al. | 606/139 |
| 5,061,274 | 10/1991 | Kensey | 606/213 |
| 5,108,421 | 4/1992 | Fowler | 606/213 |
| 5,129,882 | 7/1992 | Weldon et al. | 604/96 |
| 5,221,259 | 6/1993 | Weldon et al. | 604/96 |
| 5,250,055 | 10/1993 | Moore et al. | 606/148 |
| 5,281,234 | 1/1994 | Wilk et al. | 606/139 |
| 5,292,332 | 3/1994 | Lee | 606/213 |
| 5,304,184 | 4/1994 | Hathaway et al. | 606/144 |
| 5,370,660 | 12/1994 | Weinstein et al. | 606/213 |
| 5,383,896 | 1/1995 | Gershony et al. | 606/213 |
| 5,391,182 | 2/1995 | Chin | 606/144 |
| 5,443,481 | 8/1995 | Lee | 606/213 |

FOREIGN PATENT DOCUMENTS

| | | |
|---|---|---|
| 482350A2 | 4/1992 | European Pat. Off. |
| 172957 | 7/1965 | Russian Federation . |
| 9014796 | 5/1990 | WIPO . |
| 9222252 | 6/1992 | WIPO . |

*Primary Examiner*—Gary Jackson
*Attorney, Agent, or Firm*—Lockwood, Alex, Fitzgibson & Cummings

[57] ABSTRACT

A wound closure apparatus and a method for its use are described. The apparatus includes a trilumen tubular member dimensioned to be positioned within a blood vessel through a conventional catheter sheath introducer. A mesh assembly extends longitudinally through the center lumen of the tubular member to position an expandable mesh portion within the vessel. The expandable mesh portion can be configured between a collapsed condition and an expanded condition by the attending surgeon or other medical personnel. Sutures are deposited into the blood vessel by a pair of medical needles inserted through the vessel wall adjacent the wound so that the leading ends of the sutures are deposited directly into the expandable mesh portion and are captured therein. The leading ends of the sutures can be withdrawn from the vessel through the center lumen of the trilumen body and pulled outside of the wound area where the surgeon can tie the ends thereof to close and seal the vessel wound.

26 Claims, 4 Drawing Sheets

WOUND CLOSURE APPARATUS AND METHOD FOR ITS USE

The invention relates to a surgical instrument and a method for its use. More specifically, the invention relates to a surgical method and a related device for suturing a puncture or surgical incision in a blood vessel within the body of a living patient. The device and method of the present invention include a means for inserting suture material through the tissue wall adjacent the incision or puncture as well as additional means for withdrawing the suture material back out through the puncture so that the ends of the suture can be tied and the wound or incision thereby closed.

BACKGROUND OF THE INVENTION

Some medical procedures require surgical access into the vascular system through an artery or other vessel using, for example, a conventional catheter sheath introducer or dilator for the insertion of certain instruments for both therapeutic and diagnostic procedures. Medical Instruments such as guide wires, catheters, balloon angioplasty devices or the like are typically inserted into the vascular system through a sheath introducer positioned with its distal end extending through a vessel wall. Once the device gains access into the vascular system, it can be advanced to the area requiring a specific medical procedure. The conventional sheath introducer typically has a relatively large outer, diameter, resulting in a correspondingly large wound within the wall of the vessel which must be closed and sealed after the procedure is completed.

It is generally desirable to prevent further bleeding from the blood vessel by sealing the wound as quickly as possible. One common technique to prevent further bleeding is through the application of continuous pressure on the wound until the patient's blood clots sufficiently to seal the vessel. One problem with this common technique, however, is that the application of pressure often requires the dedication of an hour or more of time by the attending medical personnel. Even with such dedicated medical attention, a hematoma can still occur if the patient moves during the clotting process. As a result of these problems, patients can be required to stay at least one night in a hospital for rest and observation. The additional hospital stay is an inconvenience for the patient which also increases the cost associated with the particular medical procedure.

Other instruments for closing surgical wounds and the like are known. These devices typically insert a plug-like object or a clotting agent within the wound area to seal the vessel. The plug or clotting agent can be positioned either within the vessel or outside of the vessel and in close proximity to the outer vessel wall. Various types of plugs have been proposed. For example, collagen plugs are common and are typically designed to be placed outside of the vessel and near the opening within the vessel wall. Somewhat more elaborate plugs have also been proposed for placement directly within the vessel, with the plug secured against the inner vessel wall or lumen by an external suture extending into the wound and attached to the plug. Still other devices accomplish the placement of a clotting agent within the wound area, dispensing a foam, powder or gel within the wound from the distal end of an application device.

A basic shortcoming of the aforementioned instruments is that their use often requires or results in the deposition of plugs or clotting agents within the vessel. This can be unintentional but, even in those instances where the deposition of a plug is to be outside of the vessel, the attending physician may encounter positioning problems so that the plug inadvertently protrudes at least partially into the vessel. Alternatively, the plug may slip into the vessel during the healing process due to the application of external pressure on the wound. In turn, these plugs or clotting agents can partially occlude the flow of blood through the vessel at the site of the original wound, possibly leading to complications such as thrombosis or stenosis. It would be desirable, therefore, to provide an apparatus which avoided the problems and shortcomings of the prior art techniques and devices for closing wounds or incisions within blood vessel in a living patient. Although sutures are very effective generally in closing and sealing surgical wounds, the art has failed to provide an instrument and a method for its use which utilize sutures to close a wound or incision within a vessel. Accordingly, it would be desirable to provide such an apparatus and method which would facilitate the proper placement of sutures within a vascular wound to allow the surgeon or attending medical personnel to quickly and efficiently close and seal such a wound. Most preferably, it is desirable to provide such an apparatus and method which can be used in conjunction with existing medical equipment such as conventional catheter sheath introducers, for example.

Accordingly, it is a general object of the present invention to provide a wound closure apparatus and a method for closing vascular wounds, including surgical wounds.

It is a further object of the invention to provide a wound closure apparatus and a method for its use which facilitate the proper placement of sutures for the closure of vascular wounds.

It is still another object of the invention to provide a wound closure apparatus and a method for its use which can be used with conventional medical equipment such as a catheter sheath introducer, for example.

BRIEF DESCRIPTION OF THE INVENTION

The wound closure apparatus of the present invention overcomes the shortcomings of the prior art and achieves the aforementioned objectives by providing a device including a trilumen tubular member dimensioned to be positioned within a catheter sheath introducer. The tubular member is provided with a center lumen extending from its proximal end to its distal end. A mesh assembly is configured to extend through the center lumen of the tubular member and includes an expandable mesh portion constructed of a set of flexible filaments which are capable of being configured between an expanded condition and a collapsed condition. A leading coil is affixed to the distal end of the expandable portion to provide the attending physician with a means for sensing when the expandable mesh portion is properly positioned within a blood vessel. The mesh assembly also includes a shaft which, when the assembly is within the center lumar of the tubular member, is of sufficient length to extend from at least the proximal end of the tubular member through the center lumen and to the expandable portion. The stem member includes an outer sheath and an inner control cord extending axially through the outer sheath. The control cord is axially slidably moveable within the sheath and is affixed to one end of the expandable portion to provide a means to configure the expandable portion between its expanded condition and its collapsed condition.

The trilumen tubular body also includes first and second side lumens positioned generally parallel to the aforementioned center lumen and extending longitudinally along opposing sides thereof. The side lumens are each dimensioned to slidably receive a needle or other piercing element and to thereby deliver a pair of sutures within the vessel being treated. In the arrangement of parts described herein, the needles or piercing elements are aligned to puncture the vessel wall on opposing sides adjacent the wound to thereby deliver sutures into the vessel through the vessel wall. The expandable mesh, when configured in its expanded condition, is constructed to trap the distal ends of each of the sutures ejected from the needles into the vessel. The mesh and the sutures trapped therein can then be withdrawn from the vessel through the center lumen and pulled outside of the patient's body. Accordingly, the suture material will then extend through the vessel wall on either side of the original wound, into the vessel and back out through the original wound where the surgeon can tie the ends of the suture material into a suitable knot for closing and sealing the punctured vessel.

Those skilled in the art will more fully appreciate the scope of the present invention as well as the structural details of its preferred embodiment upon further consideration of the remainder of the disclosure including the detailed description of the preferred embodiment and the appended claims.

BRIEF DESCRIPTION OF THE DRAWINGS

In describing the details of the preferred embodiment of the present invention, reference will be made to the various figures wherein.

DETAILED DESCRIPTION OF THE PREFERRED EMBODIMENTS

The present invention provides a novel wound closure instrument as well as a method for the use of the instrument. The disclosed instrument is a useful surgical tool for applying sutures to a wound within a vessel following a procedure such as an angioplasty, for example, where the vessel has been surgically opened to insert a balloon catheter and the like. The apparatus of the invention can be inserted into the vessel through a conventional catheter sheath introducer and is constructed to allow the surgeon to insert a pair of sutures through the vessel wall on adjacent sides of the wound. A mesh assembly is provided to capture the free ends of the sutures within the vessel to allow the attending physician to then withdraw the captured sutures from the vessel back through the wound and outside of the patient's body where they can then be appropriately tied to close and seal the wound.

In discussing the structural features of the preferred embodiment of the present invention, reference is now made to the various figures wherein the structural elements are identified with reference numerals, all of which are discussed herein. Referring now to the Figures, a wound closure apparatus 10 is provided and, in FIG. 1, the component parts and their interrelationship is illustrated. The instrument 10 includes an elongate tubular member 12 having three separate lumens extending from the proximal end 14 to the distal end 16 thereof. An elongate mesh assembly 18 is provided and is dimensioned to fit within and extend axially through the center lumen 40 (e.g. FIG. 2) of the tubular member 12. The assembly 18 includes an elongate tubular outer sheath 26 having an inner lumen to receive a control cord 28 which extends through the sheath 26 and is axially slidable therein. A first hub or cap 30 is provided at the proximal end of the outer sheath 26 and a second hub or cap 32 is provided at the proximal end of the control cored 28. Both of the hubs or caps 30 and 32 include gripping surfaces thereon. The caps 30 and 32 provide a manually operable means for the control and operation of the mesh assembly 18, as is discussed herein. The control cord 28 extends from the proximal end 20 of the mesh assembly 18 and through the outer sheath 26 to the distal end 22 where the cord 28 is affixed to the expandable mesh portion 34.

The expandable mesh portion 34 is preferably composed of flexible filaments which are anchored at their respective ends along first and second collars 37 and 39, respectively. The first collar 37 is preferably affixed to the surface of the outer sheath 26 at the distal end thereof. The second collar 39 is affixed to the distal end of the control cord 28. By the selective axial movement of the control cord 28 within the outer sheath 26, the expandable mesh portion 34 can be configured in a collapsed condition where the filaments are extended to substantially their maximum longitudinal extent (FIGS. 1 and 2), and an expanded condition where collars 37 and 39 are brought into close proximity to bend the filaments and bow the mesh portion 34 (FIG. 3). The mesh 34 is configured between these two conditions by the relative movement of the control cord 28 within the outer sheath 26 with the mesh 34 being constructed to assure the aforementioned collapsed condition as a preferred configuration.

The tubular member 12 includes first and second side lumens 42 and 44, respectively (e.g. FIG. 2) which are disposed parallel to and on either side of the center lumen 40. The center lumen 40 as well as the first and second side lumens 42 and 44 extend from the proximal end 14 of the tubular member 12 to the distal end 16 thereof. The center lumen 40 is dimensioned to receive the mesh assembly therein with the expandable mesh portion 34 in its collapsed condition. The first side lumen 42 and the second side lumen 44 are dimensioned to slidably receive a piercing member such as first and second needles 46 and 48. The two needles 46 and 48 are both hollow and are of a sufficient gauge to receive sutures 66 and 68 therein.

Plungers 74 and 76 are provided to push the sutures through the lumen of the needles 46 and 48. The plungers 74 and 76 may be, in fact, a cannula, a solid wire or other rod-like member suitable for advancing the sutures 66 and 68 through the first and second needles 46 and 48, respectively. Each of the plungers 74 and 76 are provided at one end thereof with caps 78 and 80 to allow the user of the apparatus 10 to hold and manipulate the plungers 74 and 76. The caps 78 and 80 also serve as stops to limit the extent to which the plungers 74 and 76 can be longitudinally advanced within the lumens of the needles 46 and 48.

Preferably, the plungers are of sufficient length to span the length of the needles 46 and 48 to push the sutures just past the pointed ends 54 and 56 and into the expanded mesh portion 34. The guide tips 70 and 72 on the sutures 66 and 68 are optional to allow the sutures to be more easily advanced through the needles 46 and 48 by the sliding action of the plungers 74 and 76. Of course, those skilled in the art will appreciate that a knot or other comparable structure or device will operate as functional and structural equivalents to the guide tips 70 and 72.

The basic structure of the apparatus 10 of the present invention has been discussed and described above. Accordingly, its operation will now be described with reference to the structural members already identified. Referring generally to FIGS. 2–5, the basic operation of the apparatus 10 is illustrated in its various stages of use. The apparatus 10 is inserted into a wound within the vessel wall 60 of the vessel 58 by use of a conventional catheter sheath introducer (CSI) 38 as shown in FIG. 2. As is known by those skilled in the art, the CSI 38 is used to facilitate the insertion of a variety of instruments for diagnostic and therapeutic use within the vascular system.

Initially, the CSI is inserted within the wound in the vessel wall 60. The tubular member 12 is then inserted within the CSI to protrude into the vessel 58 at the distal end 16 thereof. The CSI 38 is then withdrawn over the tubular member and the mesh assembly 18 is inserted into the center lumen 40 to position the expandable mesh portion 34 within the vessel 58. The leading coil 36 provides a means for alerting the attending physician that the expandable mesh portion 34 is positioned within the vessel 58. The leading coil 36, when the mesh assembly is within the vessel 58, will abut the vessel lumen 62 thereby creating a resistance against the further advancement of the mesh assembly 18.

Once the expandable mesh portion is properly positioned within the vessel 58, as shown in FIG. 2 for example, the trilumen tubular member 12 can be partially withdrawn so that its distal end 16 is retracted from the wound and repositioned adjacent to the outer vessel wall 60 without protruding into the wound. At this stage of operation, the expandable portion 34 of the mesh assembly 18 is in its unexpanded or collapsed condition wherein the individual filaments of the mesh portion 34 are in their fully extended state with the first and second collars 37 and 39 at the greatest possible distance from each other within the structure of the instrument 10.

As shown in FIG. 3, when the distal end 16 of the tubular member 12 is positioned outside of the vessel wall 60, the expandable mesh portion 34 can be reconfigured to its expanded condition by axially sliding the control cord within the outer sheath 26 of the mesh assembly 18 to pull the second collar 39 toward the first collar 37. The caps 30 and 32 are provided with gripping surfaces to allow the attending physician or other medical personnel to configure the expandable portion 34 by pulling the cap 32 affixed to the control cord 28 axially away from the cap 30 affixed to the outer sheath 26. When the expandable portion 34 is configured in its expanded condition, as shown in FIG. 3 the ends of the fibers thereof are in close proximity to one another and the member 34 expands to a width equal to or greater than the cross-sectional diameter of the tubular member 12. When the expandable portion 34 is fully expanded, the first and second collars 37 and 39 are positioned substantially adjacent one another and the fibers of the expandable portion 34 assumes a configuration where at least a portion of the expanded fibers are substantially perpendicular to the longitudinal axis of the control cord 28.

Once the expandable mesh portion 34 is in its expanded condition, the relative position of the mesh assembly is adjusted to position the mesh portion 34 adjacent the wound so that the fibers of the mesh portion 34 are at least partially in contact with the inner lumen 62 of the vessel wall 60. Proper positioning of the expandable mesh 34 can be accomplished by retracting the outer sheath using the gripping surface on the cap 30. As those skilled in the art will appreciate, the relative positioning of the caps 30 and 32 must be maintained during this step to maintain the mesh 34 in its expanded condition. The mesh assembly 18 is axially adjusted by advancing the mesh portion 34 toward the distal end 16 of the tubular member 12 until the operator experiences resistance to any further movement caused by the expanded mesh 34 when it abuts the lumen 62 of the vessel wall 60.

Figures 4, 5:
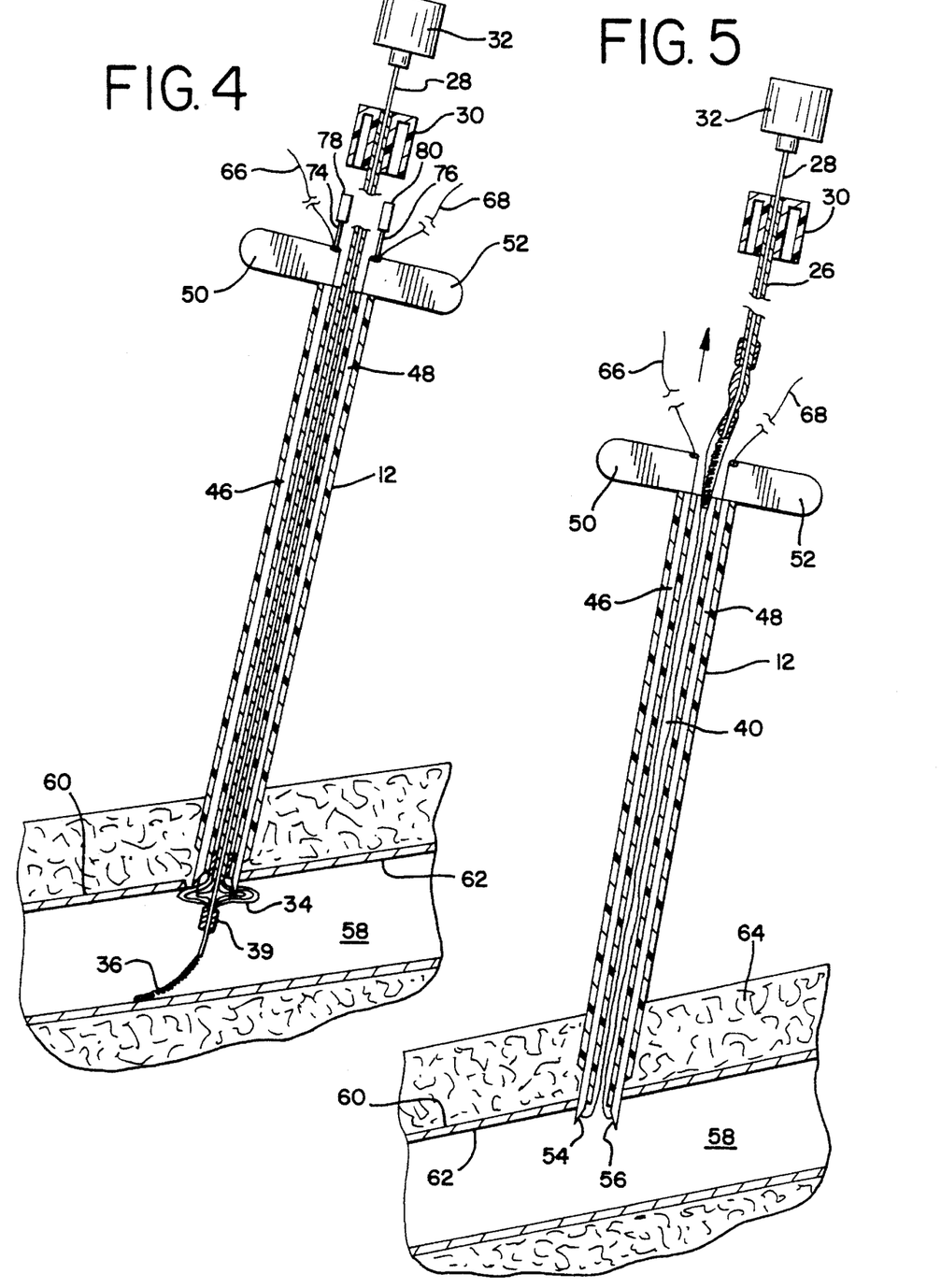
FIG. 4 is another side elevational view, in cross section, of the wound closure device at yet another stage of its operation.
FIG. 5 is a side elevational view, in cross section, of the wound closure device of the present invention at still another stage of its operation.

Referring generally to FIGS. 3 and 4, the first and second needles 46 and 48 are next advanced through the first and second side lumens 42 and 44, respectively. The pointed ends 54 and 56 on the needles 46 and 48 are advanced through the wall 60 of the vessel 58 to protrude therethrough and into the vessel 58 on adjacent sides of the original wound. The needles 46 and 48 are provided with wing members 50 and 52, respectively, at the proximal ends thereof and the needles are advanced to their fullest extent into the side lumens 42 and 44. When the tubular member 12 is properly positioned, the needles are of sufficient length to penetrate the vessel wall 60 substantially as shown in FIG. 4 to advance the points 54 and 56 into the mesh 34. It should be noted that the orientation of the needle points 54 and 56 is preferably such that the openings of the needles are oriented inwardly to open toward the center lumen 40. The wings 50 and 52 provide gripping surfaces and are preferably oriented on the needles 46 and 48 so that the outward orientation of the wings 50 and 52, as shown in FIG. 3, when the needles are disposed within the side lumens 42 and 44 will serve as an indicator that the needle points 54 and 56 are oriented in a preferred manner.

With the needles 46 and 48 fully inserted within the side lumens 42 and 44, sutures 66 and 68 can be advanced through the needles from the proximal ends thereof to the points 54 and 56 to deposit the leading ends of the sutures 66 and 68 within the expanded mesh member 34. To facilitate the advancement of the suture 66 and 68 through the needle lumens, plungers 74 and 76 may be provided. Preferably the plungers 74 and 76 are each of sufficient length to travel the full longitudinal extent of the needles. Cap members 78 and 70 are provided at the proximal ends of the plungers 74 and 76 to operate as stop members when the plungers are fully advanced within the lumen of the needles 46 and 48.

Figure 1:
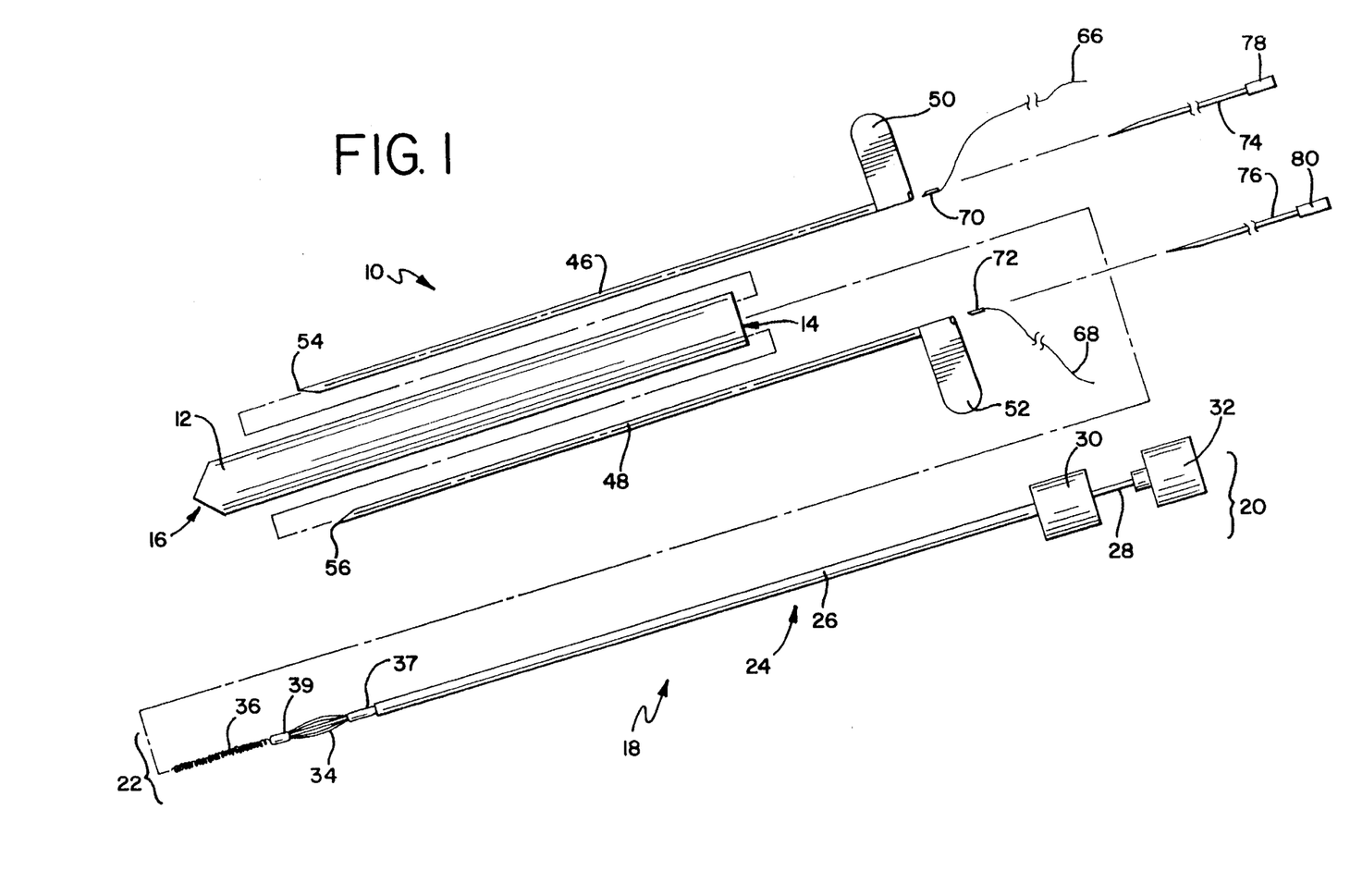
FIG. 1 is an exploded perspective view of a wound closure device according to the present invention.
Figures 2, 3:
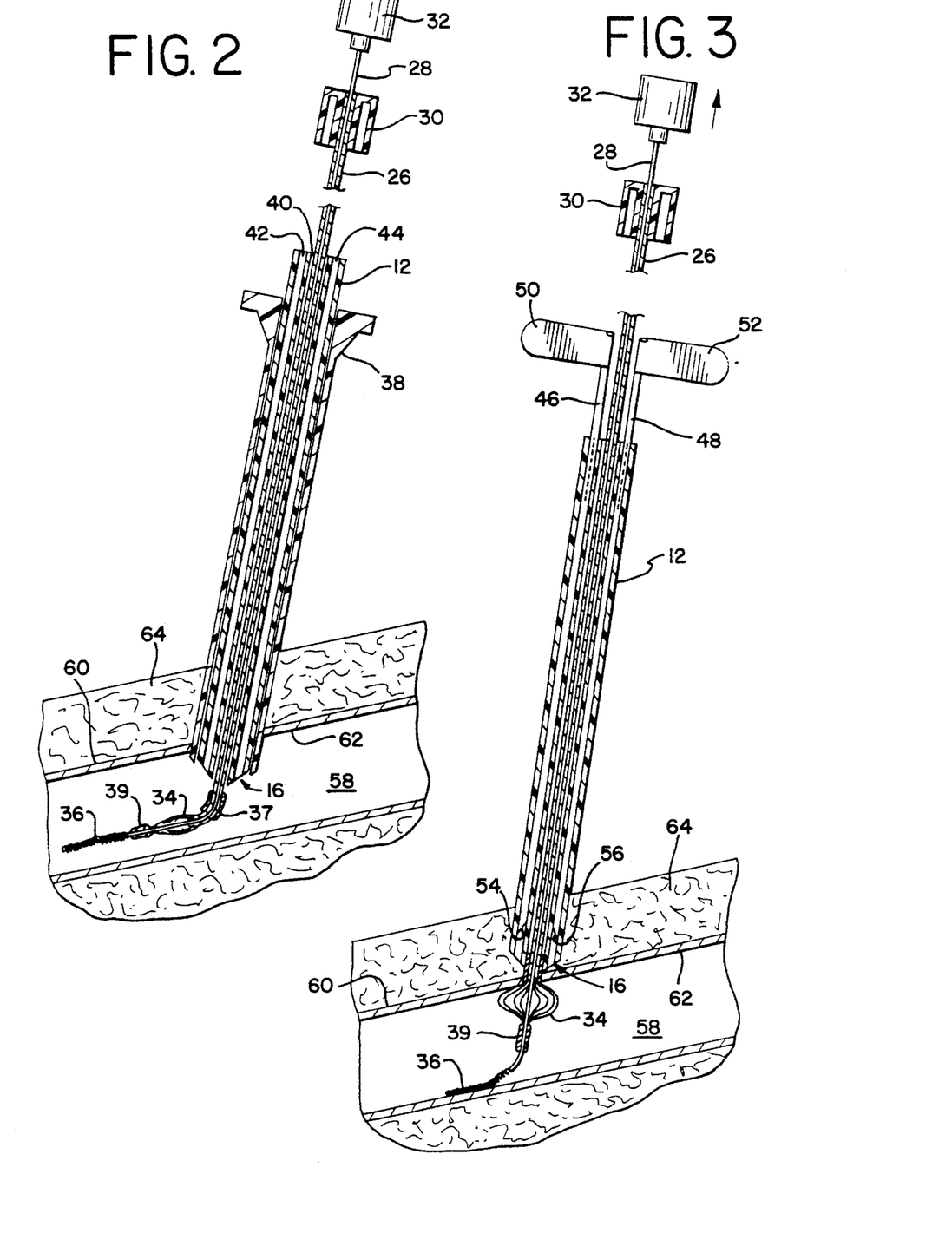
FIG. 2 is a side elevational view, in cross-section, illustrating the operation of the wound closure device of the present invention.
FIG. 3 is another side elevational view, also in cross section, of the wound closure device of the present invention in another stage of its operation.

The ends of the sutures 66 and 68 can be provided with guide tips 70 and 72, substantially as shown in FIG. 1, for example. Alternatively, the ends of the sutures can be knotted to provide a means by which the ends of the sutures 66 and 68 can be easily pushed along the length of the needle lumen by the plungers 74 and 76. With the plungers 74 and 76 fully advanced within the needles 46 and 48, the ends of the sutures 66 and 68 are deposited near or within the mesh portion 34 in its expanded condition. The sutures can be further secured within the fibers of the mesh portion by rotating the entire mesh assembly 18, including the mesh portion 34 around the longitudinal axis thereof.

With the leading ends of sutures 66 and 68 advanced through the needles and captured within the expanded mesh portion 34, the mesh portion 34 can then be reconfigured to its collapsed orientation by advancing the control cord 28 axially within the outer sheath 26 so that the hub 32 is advanced toward the hub 30 and the first and second collars 37 and 39 are again positioned at their greatest distance from each other. Once the expandable mesh portion 34 is reconfigured, it may then be withdrawn from the vessel 58 through the wound and back through the center lumen 40 of the tubular member 12. With the distal ends of the sutures 66 and 68 trapped within the expandable mesh portion 34, the aforementioned withdrawal of the mesh 34 through the center lumen further advances the suture material 66 and 68 through the needles 46 and 48 and back up through the center lumen, substantially as shown in FIG. 5. In this manner, the suture material is threaded first through the vessel wall 60 adjacent the original wound and into the vessel 58, from which it is pulled back up through the original wound and outside the body of the patient.

Figure 6:
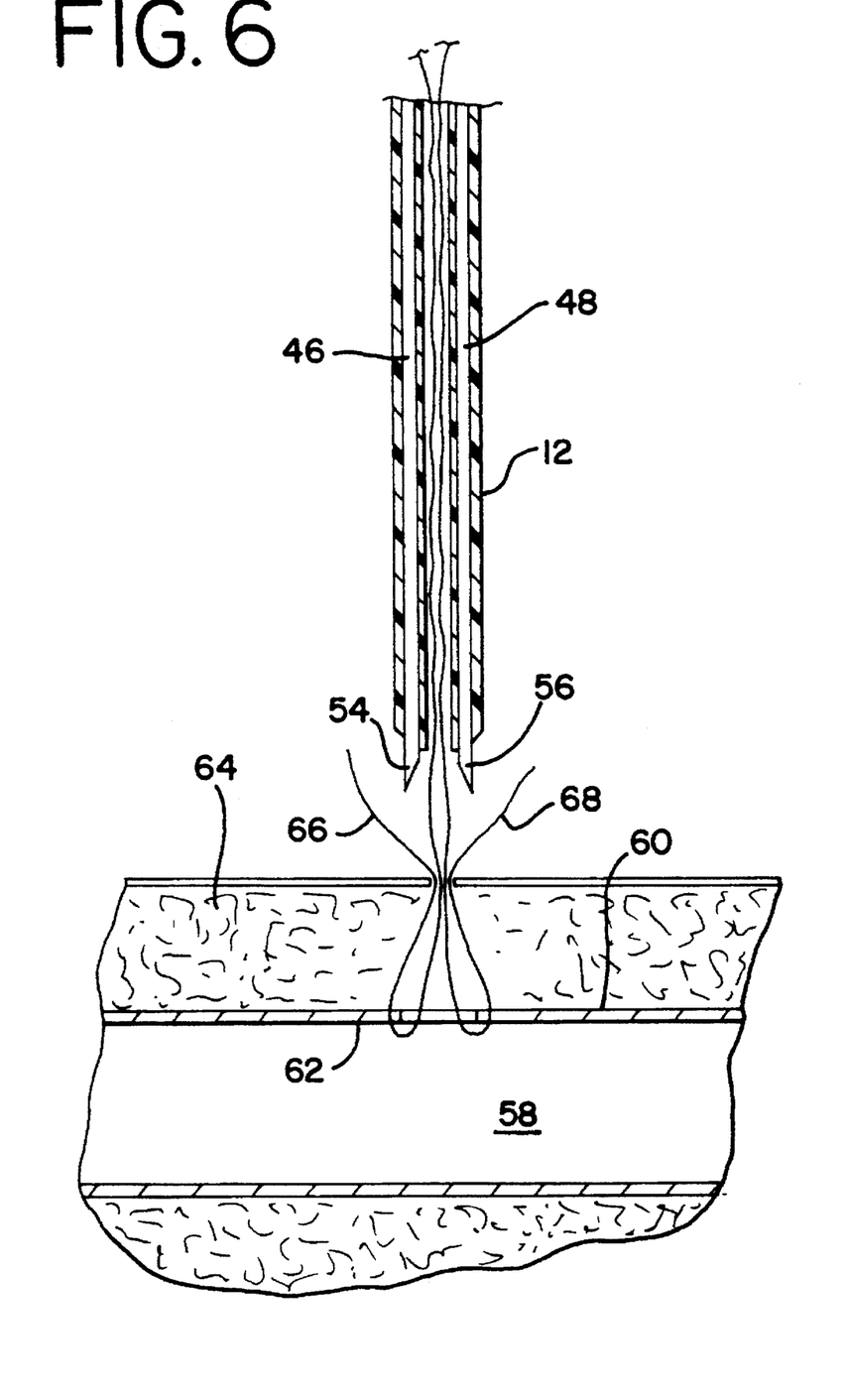
FIG. 6 is a side elevational view, in cross section, of the wound closure device of the present invention in a final stage of its operation.

With the suture material advanced as described herein, the tubular member 12 and the needles 46 and 48 can be withdrawn from the patient. FIG. 6, for example, illustrates a final stage of the process of the present invention with the tubular member 12 so withdrawn. At this stage, the ends of the sutures 66 and 68 can be detached by cutting, for example, from the needle tips 54 and 56. When the tubular member 12 is fully withdrawn from the wound, the portions of the sutures 66 and 68 extending through the center lumen 40 can also be detached therefrom to provide the attending physician or medical personnel with a set of sutures which are properly positioned within the wound and which may then be used in a known matter to close and seal the vessel wall 60.

It will be appreciated that the relative positioning between the mesh portion 34 and the needle points 54 and 56 is not limited to the preferred positioning described above. Where the needle points 54 and 56 are not directly positioned within the expanded mesh portion 34, the sutures can still be captured within the mesh portion 34 by the rotation thereof about the longitudinal axis of the mesh assembly 18. Preferably, the filaments within the expandable mesh portion 34 are twisted somewhat in their orientation between the first collar 37 and the second collar 39 so that each of the filaments spans a twisted path between the first collar 37 and the second collar 39. Although other configurations are within the scope of the invention, the aforementioned configuration for these filaments is at least one preferred way to provide a structure which will efficiently and easily capture the ends of the sutures inserted into the vessel through the needles 46 and 48.

Regarding materials, the tubular member is preferably manufactured of a suitable biocompatable polymeric material such as a polyurethane, for example. The mesh assembly 18 can be made from a variety of suitable materials. The outer sheath, for example can be made using stainless steel tubing or a suitably rigid polymeric material. The control core 28, similarly can be manufactured from a polymeric material or a stainless steel wire, for example. The caps 30 and 32 are of standard construction, typically made from a polymeric material such as a polyurethane, polycarbonate, nylon or polyurethane, for example. The expandable mesh portion is preferably made of resilient wire fibers which can withstand being configured between the aforementioned expanded configuration and the collapsed configuration without breaking or other substantial damage. The leading coil 36, likewise, is manufactured using a metallic coil member which is resilient and pliable to provide a means for determining the proper positioning of the mesh assembly within a blood vessel and without damaging the lumen of the blood vessel when the coil 36 makes contact therewith. Each of the needles 46 and 48 are preferably standard hollow point medical needles which are commercially available. The plungers 74 and 76 can be manufactured of any suitable polymeric or metallic material. The plunger 74 and 76 can be a cannula or can be a solid member including a wire, for example.

While a preferred embodiment of the present invention has been discussed and described herein those skilled in the art will understand that changes to the structure of the described apparatus and the method for its use can be made without departing from the true spirit and scope of the present invention as defined in the following claims.

We claim:

1. A surgical apparatus for closing an incision or wound in a vessel wall within a living patient, the apparatus comprising:
   a tubular member dimensioned for insertion within an incision, said tubular member having a proximal end and a distal end and a center lumen extending longitudinally through said tubular member from said proximal end to said distal end;
   a mesh assembly including an expandable portion, said mesh assembly dimensioned for insertion within said center lumen of said tubular member to reversibly position said expandable portion through an incision or wound into a vessel within a living patient, said expandable portion constructed to be configured between an expanded condition and a collapsed condition;
   first and second side lumens longitudinally disposed along opposing sides of said center lumen and extending along said tubular member, each said side lumen dimensioned to receive a piercing element therein;
   a pair of tubular piercing elements dimensioned to be slidably received within said side lumens, said piercing elements each having a pointed end capable of piercing the wall of a vessel to deliver first and second sutures within the vessel through the wall thereof.

2. The surgical apparatus as defined in claim 1 wherein said tubular member has an outer diameter dimensioned to be slidably received within a catheter sheath introducer.

3. The surgical apparatus as defined in claim 2 wherein said first and second side lumens extend through said tubular member from said proximal end to said distal end substantially parallel to said center lumen.

4. The surgical apparatus as defined in claim 1 wherein said mesh assembly includes a shaft of sufficient length to extend from at least said proximal end of said tubular member through said center lumen and past said distal end to position said expandable portion within said vessel, said shaft stem member including an outer sheath and a control cord positioned within said sheath and axially moveable with respect thereto, said control cord affixed at one end thereof to said expandable portion to enable said control cord to position said expandable portion between said expanded condition and said collapsed condition.

5. The surgical apparatus as defined in claim 4 wherein said mesh assembly includes means for moving said control cord relative to said outer sheath to thereby position said expandable portion between said expanded condition and said collapsed condition.

6. The surgical apparatus as defined in claim 5 wherein said expandable portion includes first and second collar members disposed axially along said mesh assembly, said first collar disposed at the distal end of said outer sheath and said second collar disposed along said control cord; said expandable portion further including a plurality of fibers extending between said first and second collars, said collars positioned adjacent one another in said expanded condition to thereby position a portion of said fibers in a substantially perpendicular orientation with respect to the longitudinal axis of said tubular member, said expandable portion having a diameter in said expanded condition greater than the diameter of said center lumen.

7. The surgical apparatus as defined in claim 4 wherein said mesh assembly further includes a leading coil extending from said expandable portion and forming the distal end of said mesh assembly.

8. The surgical apparatus as defined in claim 1 wherein said piercing elements are hollow needles having lumens extending therethrough and said apparatus further comprises at least one plunger member dimensioned to extend into the lumen of said needles to thereby guide said sutures therethrough.

9. A surgical apparatus for closing an incision or wound in a vessel wall within a living patient, the apparatus comprising:

a tubular member dimensioned for insertion within an incision, said tubular member having a proximal end and a distal end and a center lumen extending longitudinally through said tubular member from said proximal end to said distal end;

a mesh assembly including an expandable portion, said mesh assembly dimensioned for insertion within said center lumen of said tubular member to reversibly position said expandable portion through an incision or wound into a vessel within a living patient, said expandable portion constructed to be configured between an expanded condition and a collapsed condition;

first and second piercing members associated with said tubular member, each said piercing member having a proximal end and a distal end with a lumen extending therethrough, said distal end having a piercing point thereon to penetrate the wall of a vessel to deliver a suture through said piercing member lumen and within said vessel through said wall thereof.

10. The surgical apparatus as defined in claim 9, further comprising:

first and second side lumens longitudinally disposed along opposing sides of said center lumen and extending along said tubular member parallel to said center lumen, each said side lumen dimensioned to receive one of said piercing members and to position said piercing points to penetrate the wall of a vessel adjacent the wound or incision therein.

11. The surgical apparatus as defined in claim 9 wherein said tubular member has an outer diameter dimensioned to be slidably received within a catheter sheath introducer.

12. A surgical apparatus as defined in claim 10 wherein said first and second side lumens extend through said tubular member from said proximal end to said distal end substantially parallel to said center lumen.

13. The surgical apparatus as defined in claim 9 wherein said mesh assembly includes a shaft of sufficient length to extend from at least said proximal end of said tubular member through said center lumen and past said distal end to position said expandable portion within said vessel, said shaft stem member including an outer sheath and a control cord positioned within said sheath and axially moveable with respect thereto, said control cord affixed at one end thereof to said expandable portion to enable said control cord to position said expandable portion between said expanded condition and said collapsed condition.

14. The surgical apparatus as defined in claim 13 wherein said mesh assembly includes means for moving said control cord relative to said outer sheath to thereby position said expandable portion between said expanded condition and said collapsed condition.

15. The surgical apparatus as defined in claim 9 wherein said expandable portion includes first and second collar members disposed axially along said mesh assembly, said first collar disposed at the distal end of said outer sheath and said second collar disposed along said control cord; said expandable portion further including a plurality of fibers extending between said first and second collars, said collars positioned adjacent one another in said expanded condition to thereby position a portion of said fibers in a substantially perpendicular orientation with respect to the longitudinal axis of said tubular member, said expandable portion having a diameter in said expanded condition greater than the diameter of said center lumen.

16. The surgical apparatus as defined in claim 13 wherein said mesh assembly further includes a leading coil extending from said expandable portion and forming the distal end of said mesh assembly.

17. A method for closing an incision or wound in a vessel wall within a living patient, comprising:

providing a tubular member having a proximal end and a distal end thereon with a center lumen extending through said tubular member from said proximal end to said distal end;

inserting said distal end of said tubular member into a wound or incision within the wall of a vessel;

advancing an expandable mesh through said center lumen past said distal end of said tubular member and within said vessel, said mesh constructed to be configured between a longitudinally collapsed condition and an expanded condition wherein at least a portion of said mesh is substantially perpendicular to the longitudinal axis of said tubular member;

configuring said expandable mesh in said expanded condition;

delivering first and second sutures within said vessel by injecting the leading ends thereof through the wall of said vessel adjacent said incision or wound;

capturing said leading ends of said sutures within said expandable mesh; and withdrawing said expandable mesh and said leading ends of said sutures from said vessel through said wound and said center lumen of said tubular member so that said sutures are threaded first through said vessel wall adjacent said wound, into said vessel and exiting from said vessel through said wound to thereby be positioned outside of the body of a living patient where said sutures can be tied to close and seal said wound.

18. The method as defined in claim 17 wherein said providing of a tubular member further includes providing first and second side lumens extending longitudinally along opposing sides of said center lumen, each said side lumen dimensioned to receive a piercing element therein.

19. The method as defined in claim 18 wherein said delivering of first and second sutures within said vessel is accomplished using a pair of tubular piercing elements dimensioned to be slidably received within said first and second side lumens, said piercing elements each including a pointed end capable of piercing the wall of said vessel to deliver said first and second sutures within the vessel through the wall thereof.

20. The method as defined in claim 17 wherein said inserting of said distal end of said tubular member into a wound or incision is accomplished using a catheter sheath introducer to position said distal end of said tubular member within said wound.

21. The method as defined in claim 17 wherein said advancing of an expandable mesh through said center lumen is accomplished by first providing said expandable mesh as part of a mesh assembly including a shaft of sufficient length to extend from at least said proximal end of said tubular member through said center lumen and past said distal end to thereby position said expandable mesh within said vessel, said shaft member including an outer sheath and a control cord positioned within said sheath and axially moveable with respect thereto, said control cord affixed at one end to said expandable portion to enable said control cord to position said expandable portion between said expanded condition and said collapsed condition.

22. The method as defined in claim 21 wherein configuring said expandable mesh in said expanded condition includes moving said control cord relative to said outer sheath to thereby position said expandable portion between said expanded condition and said collapsed condition; said expandable portion including first and second collar members disposed axially along said mesh assembly, said first collar disposed at the distal end of said outer sheath and said second collar disposed along said control cord; a plurality of fibers extending between said first and second collars, said collars positioned adjacent one another in said expanded condition to thereby position a portion of said fibers in a substantially perpendicular orientation with respect to the longitudinal axis of said tubular member, said expandable portion having a diameter in said expanded condition greater than the cross sectional diameter of said center lumen.

23. The method as defined in claim 17 wherein said delivering of said first and second sutures within said vessel is accomplished by inserting said sutures through first and second piercing elements having lumens extending therethrough, said piercing elements including first and second plunger members dimensioned to extend into the lumen of said piercing elements to thereby guide said sutures therethrough.

24. The method as defined in claim 17 wherein said capturing of said leading ends of said sutures is accomplished by injecting the leading ends of said sutures directly into said expandable mesh once said expandable mesh is configured in said expanded condition.

25. The method as defined in claim 17 wherein said capturing of said leading ends of said sutures is accomplished by rotating said expandable mesh with respect to the longitudinal axis of said tubular member when said expandable mesh is in said expanded condition.

26. The method as defined in claim 17 wherein said withdrawing of said expandable mesh and said leading ends of said sutures includes configuring said expandable mesh into said collapsed condition prior to withdrawing said mesh member from said vessel.

\* \* \* \* \*

UNITED STATES PATENT AND TRADEMARK OFFICE
CERTIFICATE OF CORRECTION

PATENT NO.   : 5,496,332
DATED        : March 5, 1996
INVENTOR(S)  : Rolando Sierra and Lawrence A. Weinstein It is certified that error appears in the above-indentified patent and that said Letters Patent is hereby corrected as shown below:

Col. 1, line 21, "Instruments" should read --instruments--; line 28, "outer, diameter" should read --outer diameter--.
Col. 2, line 12, "within blood" should read --within a blood--; line 56, delete "lumar" and insert --lumen--.

Signed and Sealed this

Fifth Day of November, 1996

Attest:

BRUCE LEHMAN

Attesting Officer    Commissioner of Patents and Trademarks